United States Patent [19]

Morita et al.

[11] Patent Number: 4,760,145

[45] Date of Patent: Jul. 26, 1988

[54] CERTAIN 6,7-METHYLENE DIOXYDIHYDRO OR TETRAHYDRO-ISOQUINOLINE DERIVATIVES

[75] Inventors: Yoshiharu Morita, Yokohama; Naoshi Imaki, Atsugi; Hisao Takayanagi, Yokohama; Tadashi Shirasaka, Machida; Tetsuro Shimpuku, Yokohama; Yuki Takuma, Machida; Mari Oishi, Yokohama, all of Japan

[73] Assignee: Mitsubishi Chemical Industries Limited, Tokyo, Japan

[21] Appl. No.: 901,388

[22] Filed: Aug. 28, 1986

[30] Foreign Application Priority Data

Sep. 4, 1985 [JP] Japan ................................. 60-195620
Sep. 11, 1985 [JP] Japan ................................. 60-201074
Sep. 25, 1985 [JP] Japan ................................. 60-211294

[51] Int. Cl.⁴ .......................................... C07D 491/14
[52] U.S. Cl. ................................................... 546/90
[58] Field of Search .......................................... 546/90

[56] References Cited

PUBLICATIONS

Semonsky, Chem. Abstracts, vol. 46 (15), p. 7107-f-g, Aug. 10, 1952.
Krause et al., Chem. Abstracts, vol. 177, (14), Abst. No. 96785y, Oct. 2, 1972.
Goeber et al., Chem. Abstracts, vol. 78, (20), Abst. No. 124, 784-p May 21, 1973.

*Primary Examiner*—Alan L. Rotman
*Attorney, Agent, or Firm*—Oblon, Fisher, Spivak, McClelland & Maier

[57] ABSTRACT

A tetrahydroisoquinoline derivative represented by formula:

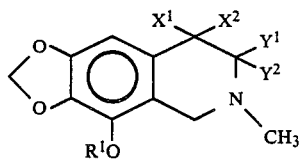

wherein $R^1$ represents hydrogen or methyl and $X^1$, $X^2$, $Y^1$ and $Y^2$ are defined as follows:

(1) $X^1$ represents —OH,

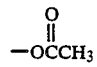

or $OR^2$ wherein $R^2$ represents lower alkyl when $X^2$, $Y^1$ and $Y^2$ represent hydrogen (2) $X^1$ and $X^2$ together form oxo (=O), when $Y^1$ and $Y^2$ represent hydrogen or (3) $Y^1$ and $Y^2$ together form oxo (=O), when $X^1$ and $X^2$ represent hydrogen which is useful as an intermediate in preparation of Cotarnine.

7 Claims, No Drawings

CERTAIN 6,7-METHYLENE DIOXYDIHYDRO OR TETRAHYDRO-ISOQUINOLINE DERIVATIVES

This invention relates to a novel tetrahydroisoquinoline derivative which is useful as an intermediate in synthesis of Cotarnine, which is a major starting material for the preparation of Tritoqualine having a pharmacological activity of antiallergy (Japanese Patent Application Laid-Open Nos. 59-44374 and 59-44382).

Hitherto, Cotarnine has been produced by oxidation of Noscapine which is a natural alkaloid (Yakugaku Zasshi, 50, 559 (1930)).

However, Noscapine is prepared from a natural product in a limited quantity, and therefore its constant supply is difficult.

We have now discovered that Cotarnine can be produced advantageously in an industrial scale by using a tetrahydroisoquinoline derivative of this invention as an intermediate in preparation of Cotarnine.

It is therefore an object of the invention to provide a novel tetrahydroisoquinoline derivative which is useful as an intermediate in preparation of Cotarnine.

The compounds of the present invention are best described by reference to the following formula I;

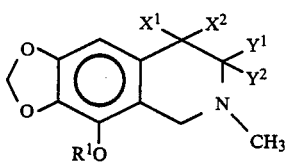

wherein $R^1$ represents hydrogen or methyl and $X^1$, $X^2$, $Y^1$ and $Y^2$ are defined as follows:

(1) $X^1$ represents —OH,

or $OR^2$ wherein $R^2$ represents lower alkyl when $X^2$, $Y^1$ and $Y^2$ represent hydrogen (2) $X^1$ and $X^2$ together form oxo (=O), when $Y^1$ and $Y^2$ represent hydrogen or (3) $Y^1$ and $Y^2$ together form oxo (=O), when $X^1$ and $X^2$ represent hydrogen The present invention will hereinafter be described in detail.

In the above-shown general formula I, $R^2$ is preferably a lower alkyl having 1 to 5 carbon atoms more preferably 1 to 3 carbon atoms, when $X^1$ represents $OR^2$ and $X^2$, $Y^1$ and $Y^2$ represent hydrogen.

Examples of the tetrahydroisoquinoline derivatives according to the invention are shown below:

4-hydroxy-8-methoxy-2-methyl-6,7-methylenedioxy-1,2,3,4-tetrahydroisoquinoline;
4,8-dimethoxy-2-methyl-6,7-methylenedioxy-1,2,3,4-tetrahydroisoquinoline;
4-ethoxy-8-methoxy-2-methyl-6,7-methylenedioxy-1,2,3,4-tetrahydroisoquinoline;
4-propoxy-8-methoxy-2-methyl-6,7-methylenedioxy-1,2,3,4-tetrahydroisoquinoline;
4-acetoxy-8-methoxy-2-methyl-6,7-methylenedioxy-1,2,3,4-tetrahydroisoquinoline;
4,8-dihydroxy-2-methyl-6,7-methylenedioxy-1,2,3,4-tetrahydroisoquinoline;
4-methoxy-8-hydroxy-2-methyl-6,7-methylenedioxy-1,2,3,4-tetrahydroisoquinoline;
4-ethoxy-8-hydroxy-2-methyl-6,7-methylenedioxy-1,2,3,4-tetrahydroisoquinoline;
4-propoxy-8-hydroxy-2-methyl-6,7-methylenedioxy-1,2,3,4-tetrahydroisoquinoline;
4-acetoxy-8-hydroxy-2-methyl-6,7-methylenedioxy-1,2,3,4-tetrahydroisoquinoline;
2,3-dihydro-8-methoxy-2-methyl-6,7-methylenedioxy-4(1H)-isoquinolone;
2,3-dihydro-8-hydroxy-2-methyl-6,7-methylenedioxy-4(1H)-isoquinolone;
1,4-dihydro-8-methoxy-2-methyl-6,7-methylenedioxy-3(2H)-isoquinolone;
1,4-dihydro-8-hydroxy-2-methyl-6,7-methylenedioxy-3(2H)-isoquinolone.

The compound of the invention can be obtained in the form of salt such as hydrochloride, sulfate, etc., depending on the preparation process.

A process for the preparation of the compound according to the invention will be illustrated below.

The compound of the general formula I in which $X^2$, $Y^1$ and $Y^2$ represent hydrogen and $X^1$ represents —OH or —$OR^2$, that is, the compound represented by the following general formula III or III';

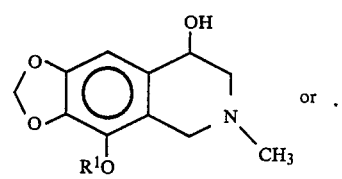

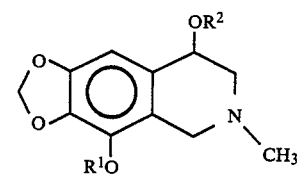

wherein $R^1$ represents hydrogen or methyl $R^2$ represents lower alkyl can be obtained by cyclization of N-methylbenzylaminoacetal represented by the following general formula II;

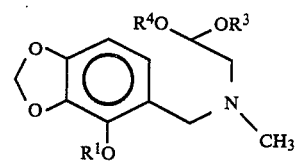

wherein $R^1$ represents hydrogen or methyl and $R^3$ and $R^4$ independently represents lower alkyl in the presence of an acid.

Examples of the acids usable in the above described cyclization reaction include hydrochloric acid, bromic acid, sulfuric acid, phosphoric acid, boron trifluoride, chlorosulfuric acid, organosulfonic acid and the like. As the organosulfonic acid, both soluble and insoluble organosulfonic acids can be used. Examples of the soluble organosulfonic acids usable in this invention include aromatic sulfonic acids such as benzenesulfonic acid, o-, m- and p-toluenesulfonic acids, o-, m- and p-xylenesulfonic acids, and aliphatic sulfonic acids such as methanesulfonic acid, ethanesulfonic acid. Examples of the insoluble organosulfonic acids include acidic cation exchange resins including those commercially available, typical examples thereof being DIAION SK-1B, DIAION PK-208, PK-216, EX-146H and PK-228L (porous type acidic cation exchange resins) and DIAION HPK-55 (highly porous type acidic cation exchange resin). DIAION is registered trade mark of gel type acidic cation exchange resin, produced by Mitsubishi Chem. Ind. Ltd.

Such acid is preferably used in an excess amount to the N-methylbenzylaminoacetal compound of the formula II. It is usually used in an amount of 1.0 to 100 moles, preferably 2.0 to 50 moles per mole of N-methylbenzylaminoacetal of the formula II.

The solvent used for the reaction in this invention is not particularly limited, but it is preferred to use a water-soluble solvent in an amount of 10 to 100,000 ml, preferably 100 to 1,000 ml to one mole of the acid.

The reaction temperature is in the range of 0° to 180° C., preferably 50° to 120° C.

The reaction is preferably carried out while removing out at least a part of the produced alcohol from the reaction system for suppressing the formation of by-products of the cyclization reaction such as 4-alkoxytetrahydroisoquinoline compound.

The alcohol can be removed, for example, (1) by a gas supply of an inert gas such as nitrogen gas through an inlet pipe provided in the reaction vessel, the produced alcohol being vapourized out together with the gas, and (2) by making the reaction system a reduced pressure condition to distill off the produced alcohol in a reduced pressure.

After completion of the reaction, the excess acid is neutralized with an alkali and then the reaction mixture is extracted with an organic solvent such as methylene chloride. Then the solvent is distilled off and recrystallized to obtain the desired compound.

The compound II can be synthesized by reacting a benzaldehyde compound represented by the following general formula IV:

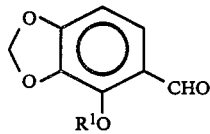

(IV)

wherein $R^1$ represents hydrogen or methyl with an aminoacetal compound represented by the following general formula V:

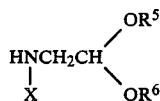

(V)

wherein X represents hydrogen or methyl and $R^5$ and $R^6$ represent lower alkyl and reducing the reaction product by using a stoichiometrical reducing agent such as $NaBH_4$ or $LiAlH_4$ or by catalytic reduction method using hydrogen.

In the above reaction, the amount of aminoacetal compound V is preferably equivalent or excess to the benzaldehyde compound IV, in the range of 1.0 to 10 moles per mole of the compound IV. A stoichiometrical reducing agent is also preferably used in an amount of equivalent to or excess of the benzaldehyde compound IV.

In the case of catalytic hydrogenation, any catalyst generally used therefor such as $PtO_2$, Pt/C, Pt/alumina, Pd black, Pd/C and Pd/alumina can by used as the hydrogenation catalyst. The preferable amount of such catalyst for hydrogenation is 0.0001 to 10% by mole of the benzaldehyde compound IV. Hydrogen may be used either under normal pressure or in a pressuirized state. Any type of solvent which is inert to the reaction can be used for the reaction.

The compound of the general formula I in which $X^2$, $Y^1$ and $Y^2$ represent hydrogen and $X^1$ is

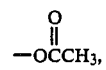

that is, the acetoxy compound represented by the following general formula VII:

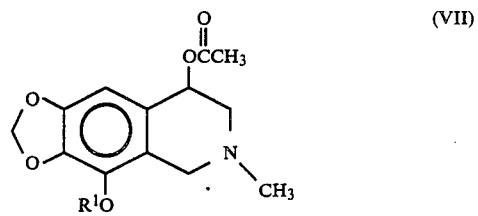

(VII)

wherein $R^1$ represents hydrogen atom or methyl group, can be synthesized by acetylating the aforementioned hydroxyl compound represented by the following general formula III;

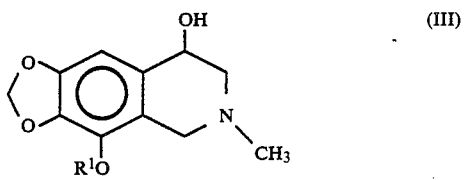

(III)

wherein $R^1$ is defined as above, with an acetylating agent.

Examples of the preferred acetylating agent include acetic anhydride and acetyl chloride, which can be preferably used in an excess amount to the compound III. The reaction can be carried out in any solvent which is inert to the reaction. The reaction temperature is preferably in the range of from −20° C. to 150° C.

After the reaction is completed, the water layer is made basic with an alkali solution and extracted with an organic solvent such as methylene chloride and then the solvent is distilled off to give the desired compound.

The isoquinolone compound of the general formula I in which $Y^1$ and $Y^2$ represent hydrogen and $X^1$ and $X^2$ jointly represent oxo =O, or the isoquinolone compound of the formula I in which $X^1$ and $X^2$ represent hydrogen and $Y^1$ and $Y^2$ jointly represent oxo =O, can be obtained by the Oppenauer oxidation of a hydroxyisoquinoline compound represented by the following general formula VI:

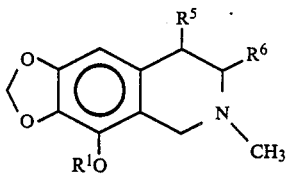

wherein R¹ represents hydrogen or methyl and one of R⁵ and R⁶ represents hydrogen while the other represents hydroxyl wherein the hydroxyisoquinoline is subjected to an intermolecular hydrogen transfer reaction by using a metal alkoxide as catalyst in the presence of a hydrogen acceptor (Org. React., 6, 207, 1960).

As a preferred example of hydrogen acceptor for the reaction, a ketone such as fluorenone and cyclohexanone is preferably used in an excess amount to the hydroxyisoquinoline compound VI. The catalyst of metal alkoxide is preferably a lower alkoxide of metal such as Na, K, Al, for example, methoxide, ethoxide, propoxide, butoxide thereof. The preferred amount of such catalyst is in an amount of 0.5 to 20 moles per mole of the hydroxyisoquinoline compound VI. The reaction is preferably carried out at the temperature of from room temperature to 150° C. in any suitable solvent which is inert to the reaction.

The thus obtained compound of the invention can serve as an useful intermediate for the preparation of Cotarnine.

The route of the preparation of Cotarnine from a tetrahydroisoquinoline derivative of the present invention is diagrammatized below:

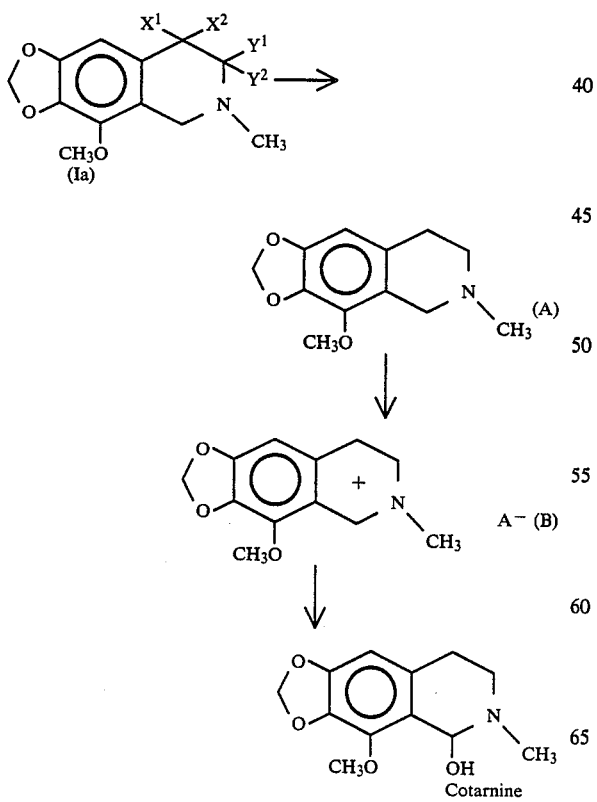

wherein X¹, X², Y¹ and Y² have the same meaning as defined in the general formula I, and A⁻ represents an anion.

As seen from the diagram illustrated above, the compound Ia, which is the compound of those having a methyl group as R¹ in the general formula I, is a precursor of the compound A, which is obtainable by the reduction of compound Ia. This reducing reaction can be taken place with hydrogen in the presence of a reducing catalyst under an acidic condition. Any reducing catalyst generally used as hydrogenation catalyst can be used for this reaction, while Pt black, PtO₂, Pt/C, Pt/alumina, Pd black, Pd/C and Pd/alumina can be mentioned as preferred examples thereof. The reaction can be taken place with an amount of 0.0001 to 10% by mole of the catalyst, preferably in acidic proton solvent, for example, mineral acid such as sulfuric acid and hydrochloric acid, and organic acid such as acetic acid and sulfonic acid. Hydrogen may be of normal pressure or pressurized. The reaction temperature is preferably in the range of from room temperature to 180° C.

After the completion of the reaction, the catalyst is removed and the excess acid is neutralized with an alkali, after which the reaction product is extracted and the solvent is distilled off to obtain the desired compound.

The compound of the general formula I in which R¹ is hydrogen can be easily converted into the compound Ia, which is the compound of the formula I having a methyl group as R¹, by methylation with a suitable methylating agent such as diazomethane. Diazomethane is preferably used in an excess amount to the starting compound I in which R¹ is hydrogen. The reaction can be preferably taken place at a temperature of from −10° C. to 100° C. in any solvent which is inert to the reaction, for example, ethyl ether.

In the above-shown preparation route, the compound A can be converted into the compound B by oxidation with an oxidizing agent of halogen type, and the compound B is hydrolyzed in an aqueous alkaline solution to obtain Cotarnine. As the oxidizing agent of halogen type, I₂, Br₂, Cl₂, NaOCl, NaOBr, NaOI and the like can be mentioned. An alcohol such as methanol and ethanol is preferably used as the solvent for the oxidation.

In this reaction route, the compound A may be converted into Cotarnine in situ, or alternatively the compound B may be once taken out and then made into Cotarnine.

The present invention will be illustrated hereinafter in further detail by way of the following specific examples, but no way limited by them and many variation can be made without departing the scope of the present invention.

REFERENCE EXAMPLE 1

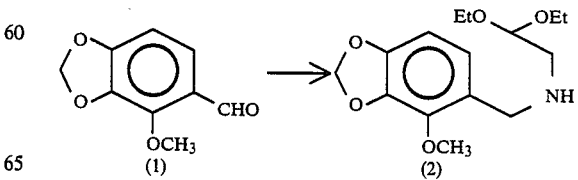

One g of platinum oxide was added to 100 ml of ethanol, and hydrogen was passed through the solution under stirring for 30 minutes. To this solution was added a solution of 54.06 g (0.3 mol) of 2-methoxy-3,4-methylenedioxybenzaldehyde (1) and 40.78 g (0.3 mol) of aminoacetaldehyde diethylacetal (2) (purity: 98%) in 100 ml of ethanol to carry out hydrogenation under stirring at room temperature for 8.5 hours. Then the catalyst was filtered out and the solvent was distilled off under reduced pressure to obtain 89.43 g of N-(2-methoxy-3,4-methylenedioxybenzyl)aminoacetaldehyde diethylacetal (2) as an oil (yield: 100%).

The resultant compound has the following IR spectrum and NMR spectrum.

IR (neat, ν max cm⁻¹): 1630, 1495, 1465, 1255.

¹H-NMR (60 MHz, in CdCl₃, δ ppm): 1.18 (6H, t, J=7 Hz, —OCH₂CH₃×2), 1.88 (1H, s, —NH), 2.68 (2H, d, J=6 Hz, NCH₂CH(OEt)₂), 3.3–3.9 (4H, m, —OCH₂CH₃×2), 3.70 (2H, s, ArCH₂N), 3.99 (3H, s, OCH₃), 4.58 (1H, t, J=6 Hz, NCH₂CH(OEt)₂), 5.87 (2H, s,

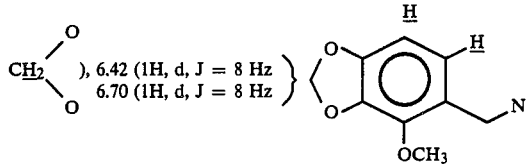

REFERENCE EXAMPLE 2

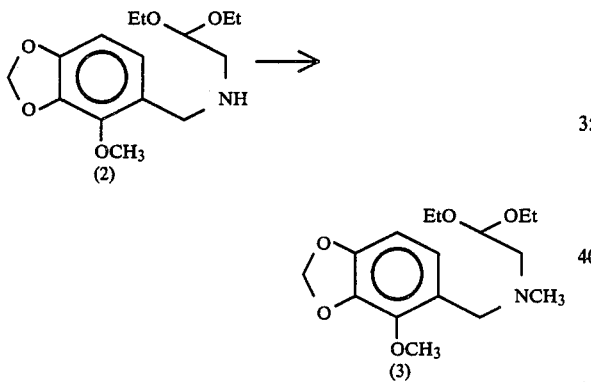

200 mg of platinum oxide was added to a solution of 15 ml of ethanol and 2 ml of acetic acid, and hydrogen was passed through the solution under stirring for 30 minutes. To this solution were added 5.95 g (20 mmol) of N-(2-methoxy-3,4-methylenedioxybenzyl)aminoacetaldehyde diethylacetal (2) and 1.89 g (22 mmol) of 35% formalin to carry out hydrogenation under stirring at room temperature for 1 hour and 45 minutes. After filtering out the catalyst, the solution was concentrated under reduced pressure and the residual oil was added with 30 ml of methylene chloride and 15 ml of water and then further added gradually with a 25% sodium hydroxide solution to make the aqueous layer basic. After separating the layers, the methylene chloride layer was washed with 15 ml of water and then dried over anhydrous magnesium sulfate. Then, the layer was filtered and concentrated under reduced pressure to obtain 6.15 g of N-(2-methoxy-3,4-methylenedioxybenzyl)-N-methylaminoaldehyde diethylacetal (3) as an oil (yield: 99%).

IR (nest, ν max cm⁻¹): 1470, 1260, 1070.

¹H-NMR (60 MHz in CDCl₃, δ ppm): 1.19 (6H, t, J=7 Hz, OCH₂CH₃×2), 2.26 (3H, s, NCH₃), 2.58 (2H, d, J=5 Hz, NCH₂CH(OEt)₂), 3.3–3.9 (4H, m, OCH₂CH₃×2), 3.52 (2H, s, ArCH₂N), 3.96 (3H, s, OCH₃), 4.63 (1H, t, J=5 Hz, —NCH₂CH(OEt)₂), 5.89 (2H, s,

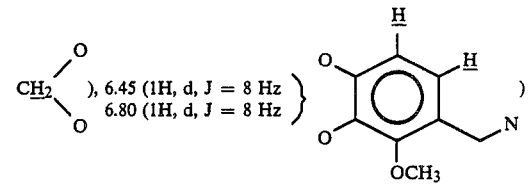

REFERENCE EXAMPLE 3

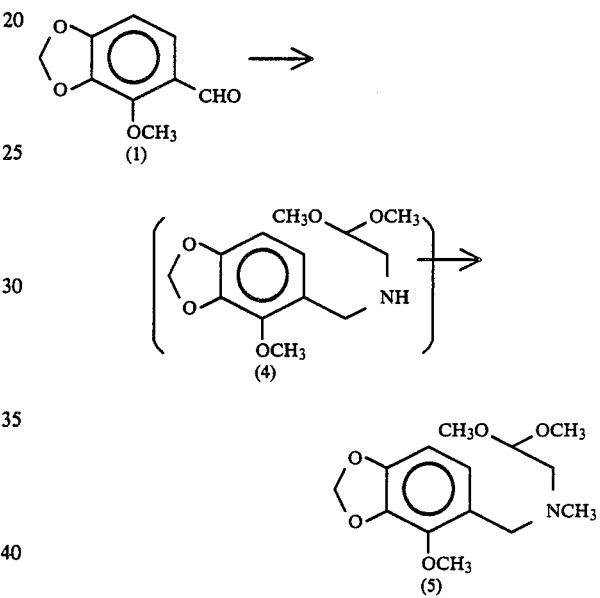

To 20 ml of methanol, 0.2 g of platinum oxide was added and then hydrogen was passed through the solution to activate the catalyst. To the solution was added a solution of 10.81 g (60 mmol) of 2-methoxy-3,4-methylenedioxybenzaldehyde (1) and 6.37 g (60 mmol) of aminoacetaldehyde dimethylacetal (99% purity) in 20 ml of ethanol to carry out hydrogenation for 3.5 hours. Then, 5.24 ml of 35% formaline (66 mmol) was added to carry out further hydrogenation for 9 hours. The catalyst was filtered out and the filtrate was concentrated under reduced pressure to obtain 16.85 g of N-(2-methoxy-3,4-methylenedioxybenzyl)-N-methylaminoacetaldehyde dimethylacetal (5) as an oil. Yield: 99%.

IR (neat, ν max cm⁻¹): 1475, 1265, 1070, 1050.

¹H-NMR (60 MHz, in CDCl₃, δ ppm): 2.26 (3H, s, NCH₃), 2.55 (2H, d, J=5 Hz, NCH₂CH(OCH₃)₂), 3.31 (6H, s, CH₂CH(OCH₃)₂), 3.49 (2H, s, ArCH₂N), 3.96 (3H, s, ArOCH₃), 4.51 (1H, t, J=5 Hz, NCH₂CH(OCH₃)₂), 5.85 (2H, s,

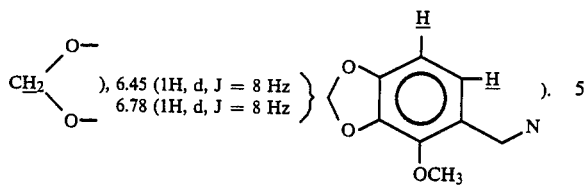

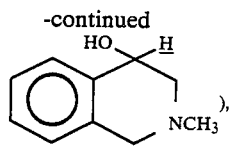

EXAMPLE 1

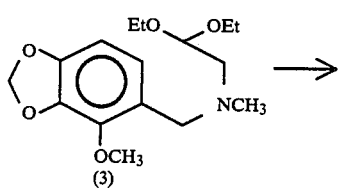

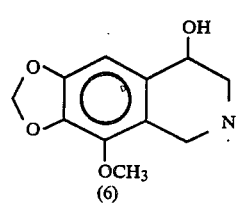

62.29 g (0.2 mol) of N-(2-methoxy-3,4-methylenedioxybenzyl)-N-methylaminoacetaldehyde diethylacetal (3) was dissolved in 400 ml of 6N sulfuric acid and the solution was stirred under heating at 76°–78° C. for 1.5 hour. The solution was cooled and added with 25% aqueous solution of sodium hydroxide at a temperature below 30° C. to make the pH of the solution about 11. Then the solution was extracted with 200 ml and then with 100 ml of methylene chloride successively. The extracts were joined, washed with 100 ml of water and then dried over anhydrous mgnesium sulfate. The salt was filtered out and the magnesium was concentrated under reduced pressure. The residue was added with 120 ml of ethanol and dissolved by heating. Then, the solution was cooled to 5° C. to be crystalized. These crystals are filtered out, washed with 30 ml of cold ethanol and dried under a reduced pressure to obtain 38.09 g of 4-hydroxy-8-methoxy-2-methyl-6,7-methylenedioxy-1,2,3,4-tetrahydroisoquinoline (m.p. 151°–153° C., yield: 80.3%).

IR (KBr, ν max cm⁻¹): 1480, 1460, 1265, 1095, 1045.
¹H-NMR (60 MHz, in CDCl₃, δ ppm):

2.38 (3H, s, NCH₃),

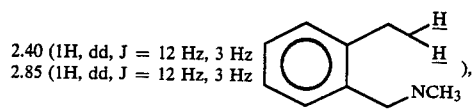

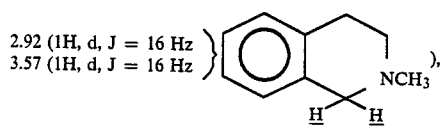

3.97 (3H, s, OCH₃),

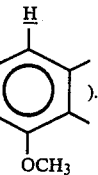

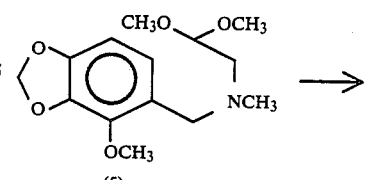

EXAMPLE 2

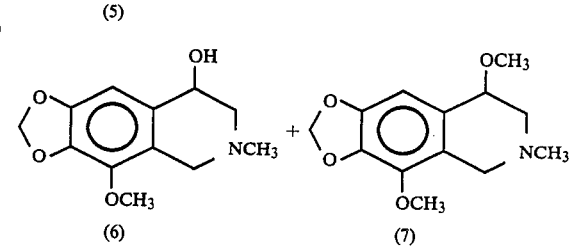

5.67 g (20 mmol) of N-(2-methoxy-3,4-methylenedioxybenzyl)-N-methylaminoacetaldehyde dimethylacetal (5) was dissolved in 40 ml of 6N sulfuric acid and the solution was stirred under heating at 76°–77° C. for 1.5 hour. The solution was cooled and added with 25% aqueous solution of sodium hydroxide at a temperature below 30° C. to make the pH of the solution about 11. The solution was extracted with 35 ml and then with 10 ml of methylene chloride successively, and the extracts were joined, washed with 20 ml of water and dried over anhydrous magnesium sulfate. The solvent was distilled off under reduced pressure and the residue was added with 12 ml of ethanol and dissolved by heating. Then, the solution was cooled to 5° C. to be crystallized. The crystals were filtered out, washed with 3 ml of cold ethanol and then dried under reduced pressure to obtain 3.71 g of 4-hydroxy-8-methoxy-2-methyl-6,7-methylenedioxy-1,2,3,4-tetrahydroisoquinoline (6). Yield: 78%, melting point: 152°–153° C.

Then the mother liquor of recrystallization was concentrated under reduced pressure and separated and purified by silica gel column chromatography (eluent: 3% methanol/chloroform) to give 0.48 g of 4,8-dimethoxy-2-methyl-6,7-methylenedioxy-1,2,3,4-tetrahydroisoquinoline (7) as an oil. Yield: 9.6%.

IR (neat, ν max cm⁻¹) of compound (7): 1480, 1270, 1085, 1050, 1040.

NMR (60 MHz, in CDCl₃, δ ppm) of compound (7):

2.48 (3H, s, NCH₃),

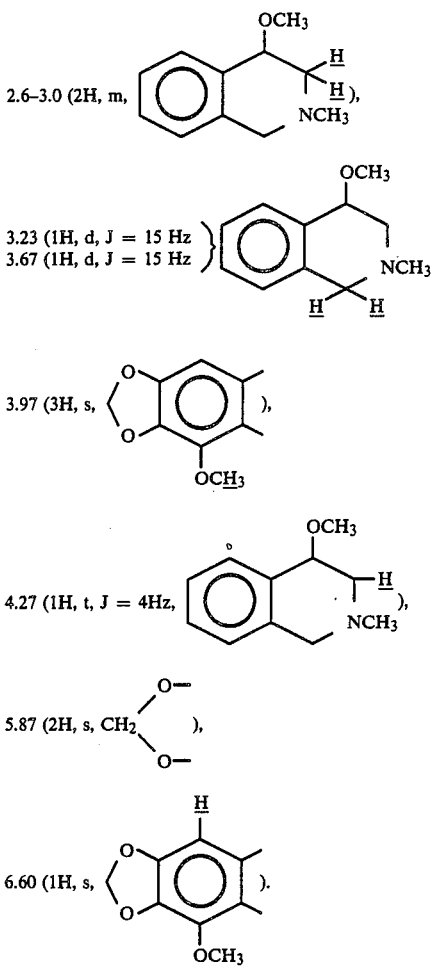

2.6-3.0 (2H, m, 3.23 (1H, d, J = 15 Hz)
3.67 (1H, d, J = 15 Hz)

3.97 (3H, s, )

4.27 (1H, t, J = 4Hz, )

5.87 (2H, s, CH₂ )

6.60 (1H, s, ).

EXAMPLE 3

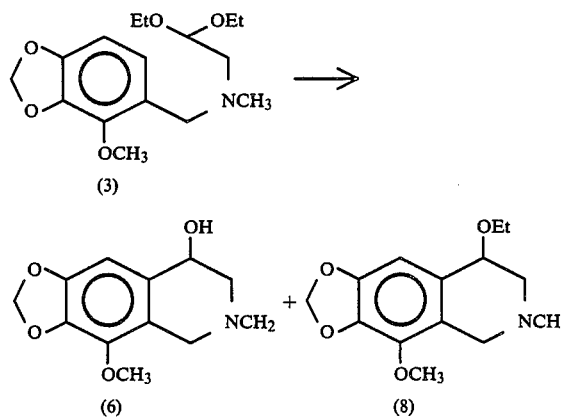

780 mg (2.5 mmol) of N-(2-methoxy-3,4-methylenedioxybenzyl)-N-methylaminoacetaldehyde diethylacetal (3) was dissolved in 1.6 ml of ethanol. The solution was added with 5 ml of 6N sulfuric acid and refluxed under heating for 2 hours and 45 minutes. After cooling, this solution was made basic by adding a 25% aqueous solution of sodium hydroxide and extracted with 5 ml and then with 2 ml of methylene chloride successively. The extracts were joined, washed with 2 ml of water and dried over anhydrous magnesium sulfate. After filtration, the solvent was distilled off under reduced pressure and the residue was separated by silica gel column chromatography to obtain 360 mg of 4-hydroxy-8-methoxy-2-methyl-6,7-methylenedioxy-1,2,3,4-tetrahydroisoquinoline (6) (yield: 61%) and 110 mg of 4-ethoxy-8-methoxy-2-methyl-6,7-methylenedioxy-1,2,3,4-tetrahydroisoquinoline (8) (yield: 17%).

COMPOUND (6)

Melting point: 153°-154° C. (recrystallized from ethanol).

IR (KBr, ν max cm⁻¹): 1480, 1460, 1265, 1095, 1045.

NMR (60 MHz, in CDCl₃, δ ppm): 2.38 (3H, s, NCH₃), 2.40 (1H, dd, J = 12 Hz, 3 Hz)
2.85 (1H, dd, J = 12 Hz, 3 Hz)
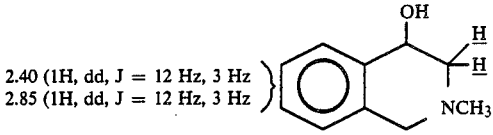

2.92 (1H, d, J = 16 Hz)
3.57 (1H, d, J = 16 Hz)
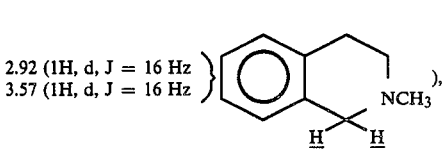

3.97 (3H, s, OCH₃), 4.42 (1H, broad S, 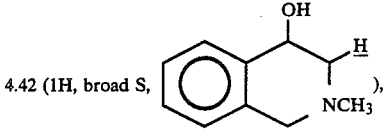

5.85 (2H, s, CH₂ 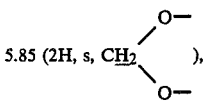 ), 6.56 (1H, s, 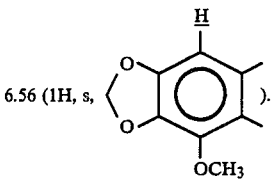 ).

COMPOUND (8)

Melting point: 52°-53° C. (recrystallized from n-hexane).

IR (KBr, ν max cm⁻¹): 1480, 1460, 1320, 1265, 1090, 1045.

¹H-NMR (60 MHz, in CDCl₃, δ ppm): 1.21 (3H, t, J=7 Hz, OCH₂CH₃), 2.41 (3H, s, NCH₃), 2.5-3.0 (2H, m, 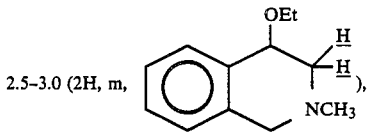 ), 3.40 (2H, s, 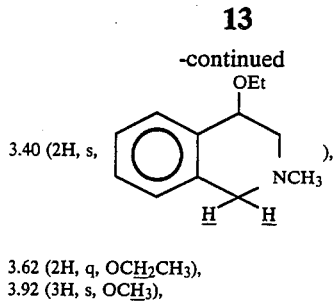), 3.62 (2H, q, OC$\underline{H}_2$CH$_3$),
3.92 (3H, s, OC$\underline{H}_3$), 4.36 (1H, t, J = 5 Hz, 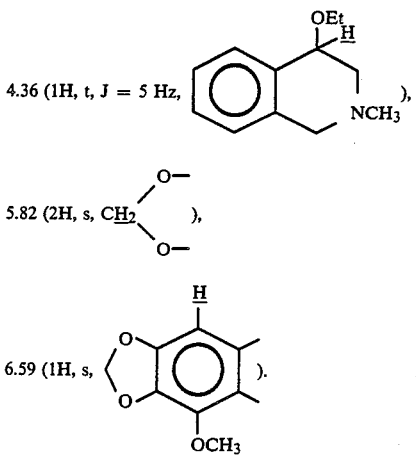), 5.82 (2H, s, C$\underline{H}_2$ $\overset{O-}{\underset{O-}{}}$ ), 6.59 (1H, s, 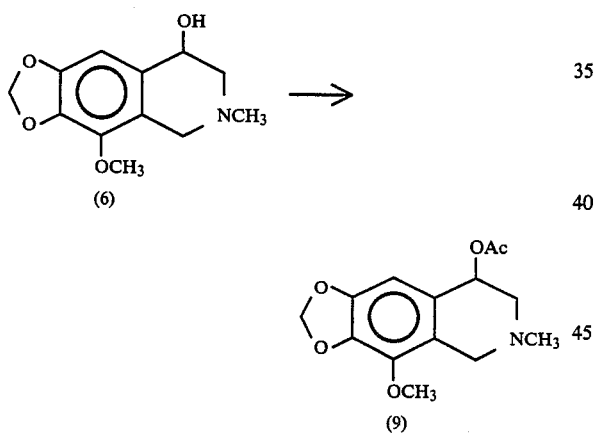 ).

EXAMPLE 4

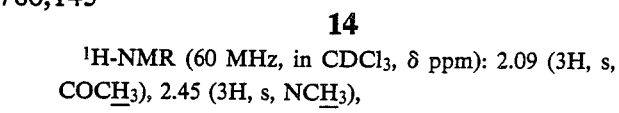

4.74 g (20 mmol) of 4-hydroxy-8-methoxy-2-methyl-6,7-methylenedioxy-1,2,3,4-tetrahydroisoquinoline (6) was dissolved in 70 ml of methylene chloride, to which 1.71 ml of acetyl chloride was added dropwise at room temperature. This solution was stirred at 20°–30° C. for one hour, added with 30 ml of water and then further added with 25% aqueous solution of sodium hydroxide to make the water layer basic. After separating the layers, the water layer was extracted with 20 ml of methylene chloride. The methylene chloride layers were joined together and washed with 30 ml of water. After drying over anhydrous magnesium sulfate, the solvent was distilled off under reduced pressure to obtain 5.53 g of 4-acetoxy-8-methoxy-2-methyl-6,7-methylenedioxy-1,2,3,4-tetrahydroisoquinoline (9) as a crystal (yield: 99%). This was then recrystallized from ethanol/n-hexane. Melting point: 109°–110° C.

IR (KBr, $\nu$ max cm$^{-1}$): 1730, 1480, 1230, 1030.

$^1$H-NMR (60 MHz, in CDCl$_3$, $\delta$ ppm): 2.09 (3H, s, COC$\underline{H}_3$), 2.45 (3H, s, NC$\underline{H}_3$), 2.5–4.0 (4H, m, 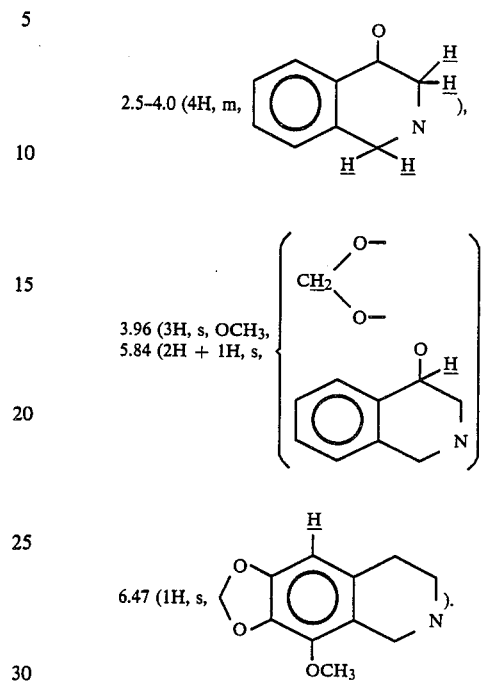 ), 3.96 (3H, s, OCH$_3$,
5.84 (2H + 1H, s, 6.47 (1H, s, ).

EXAMPLE 5

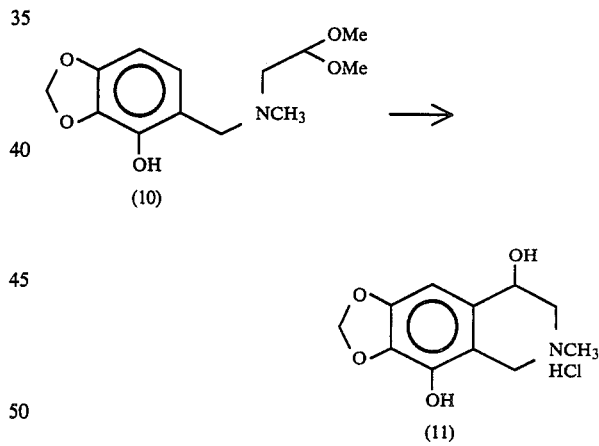

In 35 ml of 6N hydrochloric acid, 1.2 g of N-(2-hydroxy-3,4-methylenedioxybenzyl)-N-methylaminoacetaldehyde dimethylacetal (10) was dissolved and the solution was left at room temperature for 24 hours, whereupon white needlelike crystals of 4,8-dihydroxy-2-methyl-6,7-methylenedioxy-1,2,3,4-tetrahydroisoquinoline hydrochloride (11) were separated out. Melting point: 164°–166° C.

IR (KBr, disk, $\nu$ max cm$^{-1}$): 3420, 1640, 1490, 1250, 1080.

$^1$H-NMR (60 MHz, in D$_2$O, $\delta$ ppm): 2.95 (3H, s, >N$^\oplus$—C$\underline{H}_3$), 3.2–5.0 (5H, m, —C$\underline{H}_2$NC$\underline{H}_2$C$\underline{H}$O—), 5.78 (2H, s, —OC$\underline{H}_2$O—), 6.40 (1H, s, 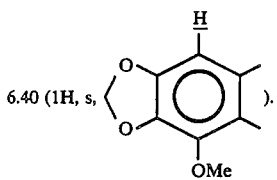 ).

EXAMPLE 6

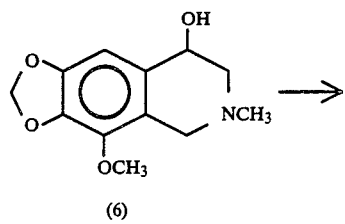

673 mg (6 mmol) of potassium-t-butoxide was added to a solution (20 ml) of 593 mg (2.5 mmol) of 4-hydroxy-8-methoxy-2-methyl-6,7-methylenedioxy-1,2,3,4-tetrahydroisoquinoline (6) and 2.25 g (12.5 mmol) of fluorenone in anhydrous benzene under a nitrogen atmosphere and refluxed under heating for 10 minutes. Then 15 ml of ice-cold water was added to the solution to stop the reaction. The solution was extracted with ethyl ether and then the organic layer was extracted with a 5% hydrochloric acid solution. The aqueous layer was made basic, then extracted with ether, dried, filtered and concentrated. The resulted residue was purified by silica gel column chromatography (eluent: 4% methanol/chloroform) to obtain 48.1 mg of 2,3-dihydro-8-methoxy-2-methyl-6,7-methylenedioxy-4(1H)-isoquinolone (12) (yield: 8%). Melting point: 116°–119° C.

IR (KBr, disk, ν max cm$^{-1}$): 1675, 1610, 1400, 1300, 1040.

$^1$H-NMR (100 MHz, in CDCl$_3$, δ ppm): 2.48 (3H, s, NC$\underline{H}_3$),

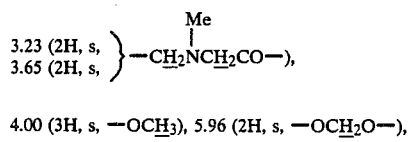

4.00 (3H, s, —OC$\underline{H}_3$), 5.96 (2H, s, —OC$\underline{H}_2$O—), 7.12 (1H, s, 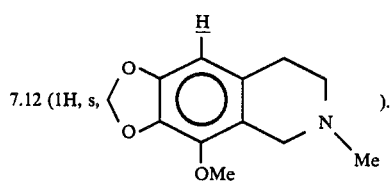 ).

COMPARISON EXAMPLE 1

Preparation of tetrahydro-4-hydroxyisoquinoline derivative 850 mg of 2-methoxy-3,4-methylenedioxy-N-methylbenzylaminodimethylacetal was dissolved in 6 ml of 6N sulfuric acid and stirred under heating at 60° C. for 3 hours in an oil bath. After completion of the reaction, the reaction mixture was treated with an alkaline solution and extracted with methylene chloride. The liquid chromatographic determination of the methylene chloride layer showed a yield of 558.6 mg (78.5%) of the desired tetrahydro-4-hydroxyisoquinoline derivative. On the other hand, the yield of the byproduced methoxy compound was 65.6 mg (8.7%).

EXAMPLE 7

Preparation of tetrahydro-4-hydroxyisoquinoline derivative with elimination of alcohol produce during reaction The process of Comparison Example 1 was repeated except that the produced methanol was removed out of the reaction system by introducing nitrogen into the system from a nitrogen blowing pipe. As a result, the desired tetrahydro-4-hydroxyisoquinoline derivative was produced in a yield of 93%, and the byproduct methoxy compound was not substantially produced.

The following Examples 8, 9 and Comparison Example 2 are of preparation of tetrahydro-4-hydroxyisoquinoline derivative by using an organosulfonic acid.

EXAMPLE 8

0.85 g (3 mmol) of 2-methoxy-3,4-methylenedioxy-N-methylbenzylaminodimethylacetal and 5.71 g (30 mmol) of p-toluenesulfonic acid were mixed with 6 ml of water and stirred in an oil bath at 80° C. for 3 hours. The reaction solution was cooled to room temperature, adjusted to a pH of up to 14 with a diluted NaOH solution and extracted with methylene chloride. The liquid chromatographic analysis of the extract showed the yield of the desired tetrahydro-4-hydroxyisoquinoline derivative was 0.626 g (88%).

The yield of the byproduced tetrahydro-4-methoxyisoquinoline derivative was 0.057 g (8%).

EXAMPLE 9

0.85 g (3 mmol) of 2-methoxy-3,4-methylenedioxy-N-methylbenzylaminodimethylacetal and 25 ml of a cation exchange resin DIAION PK-208 (having an amount of functional group of 1.2 meq/ml-R and pretreated with 2N HCl) were mixed with 12 ml of water and stirred under heating at 80° C. for 3 hours in an oil bath. The reaction mixture was cooled to room temperature, adjusted to a pH of up to 14 with a diluted NaOH solution and stirred at room temperature for 2 hours. Then the reaction solution was added with methylene chloride, extracted and filtered, and the methylene chloride layer was determined by liquid chromatography. As a result, the yield of the desired tetrahydro-4-hydroxyisoquinoline derivative was 0.517 g, which corresponds to a yield of 73%. The yield of the byproduced tetrahydro-4-methoxyisoquinoline derivative was 0.0119 g, which corresponds to a yield of 2%.

COMPARISON EXAMPLE 2

0.85 g (3 mmol) of 2-methoxy-3,4-methylenedioxy-N-methylbenzylaminodimethylacetal was mixed in 6 ml of 6N HCl and stirred under heating at 60° C. for 3 hours in an oil bath. The reaction solution was cooled to room temperature, adjusted to a pH of up to 14 with a diluted NaOH solution and extracted with methylene chloride. The liquid chromatographic analysis of this methylene chloride layer showed that the yield of the desired tetrahydro-4-hydroxyisoquinoline derivative was 0.567 g, equivalent to a yield of 80%. The yield of the byproduced tetrahydro-4-methoxyisoquinoline derivative was 0.074 g, equivalent to a yield of 10%.

REFERENCE EXAMPLE 4

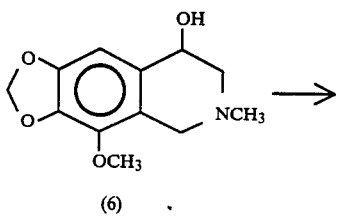

(6)

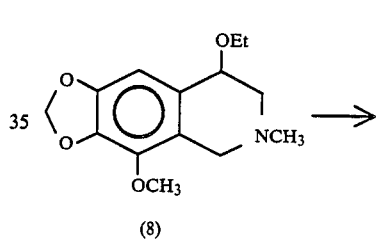

(13)

1.19 g (5 mmol) of 4-hydroxy-8-methoxy-2-methyl-6,7-methylenedioxy-1,2,3,4-tetrahydroisoquinoline (6) was dissolved in 15 ml of acetic acid, and this solution was subjected to catalytic reduction for 2 hours at 75° C. by adding 0.33 ml (6 mmol) of 97% sulfuric acid and 500 mg of 5% palladium carbon. The catalyst was filtered off, and the filtrate was added with 2 ml of 25% aqueous solution of sodium hydroxide and 5 ml of water and then concentrated under reduced pressure. The residue was added with 10 ml of water, made basic with 25% aqueous solution of sodium hydroxide under ice cooling and extracted with 10 ml and then with 5 ml of methylene chloride successively. The extract layer was washed with 5 ml of water, dried over anhydrous magnesium sulfate and concentrated under reduced pressure to obtain 1.03 g of 8-methoxy-2-methyl-6,7-methylenedioxy-1,2,3,4-tetrahydroisoquinoline. Yield: 93%.

REFERENCE EXAMPLE 5

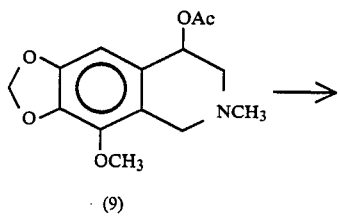

(9)

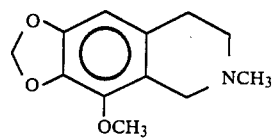

(13)

0.28 g (1 mmol) of 4-acetoxy-8-methoxy-2-methyl-6,7-methylenedioxy-1,2,3,4-tetrahydroisoquinoline (9) was added to 4 ml of ethanol. This solution was then added with 100 mg of 5% palladium carbon and hydrogenated at room temperature. After the reaction was completed, the catalyst was filtered off and the solvent was distilled off under reduced pressure. The residue was added with 5 ml of water and made basic with an aqueous solution of sodium hydroxide. The resulted solution was extracted twice with 5 ml of methylene chloride and the extract was washed with water, dried over anhydrous magnesium sulfate and concentrated under reduced pressure to obtain 0.19 g of 8-methoxy-2-methyl-6,7-methylenedioxy-1,2,3,4-tetrahydroisoquinoline (13) as a crystal. Yield: 86%.

REFERENCE EXAMPLE 6

(8)

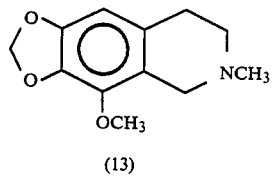

(13)

0.27 g (1.02 mmol) of 4-ethoxy-8-methoxy-2-methyl-6,7-methylenedioxy-1,2,3,4-tetrahydroisoquinoline (8) was dissolved in 15 ml of acetic acid, and the solution was added with 200 mg of 5% palladium carbon and 0.1 ml of 97% sulfuric acid and hydrogenated at 75° C. for 1 hour and 40 minutes. After cooling, the catalyst was filtered off and the filtrate was added with a small quantity of an aqueous solution of sodium hydroxide and concentrated under reduced pressure. The residue was added with 10 ml of water and made basic with an aqueous solution of sodium hydroxide. The resulted solution was extracted twice with 5 ml of methylene chloride and the extract was washed with water, dried over anhydrous magnesium sulfate and concentrated under reduced pressure to obtain 0.20 g of 8-methoxy-2-methyl-6,7-methylenedioxy-1,2,3,4-tetrahydroisoquinoline (13) as a crystal. Yield: 89%.

REFERENCE EXAMPLE 7

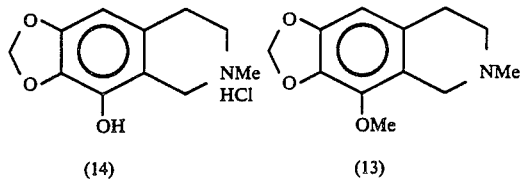

70.0 mg of 8-hydroxy-2-methyl-6,7-methylenedioxy-1,2,3,4-tetrahydroisoquinoline hydrochloride (14) was added to 28% ammonia water. Said hydrochloride was once dissolved, but recrystallized immediately. The crystals were filtered out, washed (with 28% ammonia water), dried and stirred with 4 ml of ethyl ether containing excess amount of diazomethane at room temperature to promote the reaction. As a result, the crystals were dissolved.

Five hours later, ether was distilled off to give 51 mg of 8-methoxy-2-methyl-6,7-methylenedioxy-1,2,3,4-tetrahydroisoquinoline (13) (yield: 80.0%).

REFERENCE EXAMPLE 8

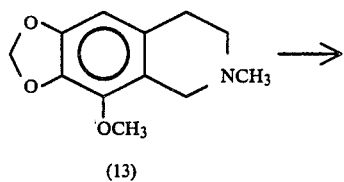

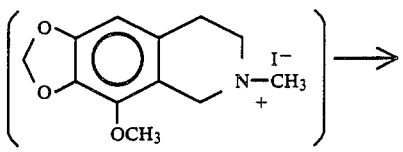

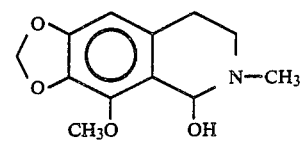

221 mg (1 mmol) of 8-methoxy-2-methyl-6,7-methylenedioxy-1,2,3,4-tetrahydroisoquinoline (13) and 108 mg (1.1 mmol) of potassium acetate were dissolved in 2 ml of ethanol. To this solution, while heating it to about 75° C., was added dropwise a solution of 254 mg (1 mmol) of iodine in 2.4 ml ethanol over a period of 85 minutes. The mixed solution was heated at 75° C. for 100 minutes and then ethanol was distilled off under reduced pressure. The residue was added with 6 ml of water and then further added with 0.6 ml of 25% aqueous solution of sodium hydroxide under ice cooling. The solution was stirred at room temperature for 30 minutes and the produced crystals were filtered out, washed twice with 0.6 ml of water and dried to obtain 217 mg of Cotarnine. Yield: 91%.

What is claimed is:
1. 4,8-Dihydroxy-2-methyl-6,7-methylenedioxy-1,2,3,4-tetrahydroisoquinoline.
2. 4-Acetoxy-8-hydroxy-2-methyl-6,7-methylenedioxy-1,2,3,4-tetrahydroisoquinoline.
3. 4-Acetoxy-8-methoxy-2-methyl-6,7-methylenedioxy-1,2,3,4-tetrahydroisoquinoline.
4. 2,3-Dihydro-8-hydroxy-2-methyl-6,7-methylenedioxy-4(1H)-isoquinolone.
5. 2,3-Dihydro-8-methoxy-2-methyl-6,7-methylenedioxy-4(1H)-isoquinolone.
6. 1,4-Dihydro-8-hydroxy-2-methyl-6,7-methylenedioxy-3(2H)-isoquinolone.
7. 1,4-Dihydro-8-methoxy-2-methyl-6,7-methylenedioxy-3(2H)-isoquinolone.

* * * * *